(12) United States Patent
Müller

(10) Patent No.: US 9,161,998 B2
(45) Date of Patent: Oct. 20, 2015

(54) METHOD AND KIT FOR PREPARING A RADIOPHARMACEUTICAL

(75) Inventor: Dirk Müller, Milda (DE)

(73) Assignee: Zentralklinik Bad Berka GmbH, Bad Berka (DE)

( * ) Notice: Subject to any disclaimer, the term of this patent is extended or adjusted under 35 U.S.C. 154(b) by 0 days.

(21) Appl. No.: 13/475,759

(22) Filed: May 18, 2012

(65) Prior Publication Data

US 2013/0310537 A1 Nov. 21, 2013

(51) Int. Cl.

| | |
|---|---|
| *C07K 1/13* | (2006.01) |
| *C07F 5/00* | (2006.01) |
| *C07F 7/00* | (2006.01) |
| *C07F 7/30* | (2006.01) |
| *C07F 19/00* | (2006.01) |
| *A61K 51/04* | (2006.01) |
| *A61K 51/00* | (2006.01) |
| *C07B 59/00* | (2006.01) |

(52) U.S. Cl.
CPC ............. *A61K 51/0482* (2013.01); *A61K 51/00* (2013.01); *C07B 59/00* (2013.01); *C07B 59/004* (2013.01); *C07B 59/008* (2013.01); *C07K 1/13* (2013.01)

(58) Field of Classification Search
USPC ........................................................ 530/345
See application file for complete search history.

(56) References Cited

U.S. PATENT DOCUMENTS 7,011,816 B2 * 3/2006 Griffiths et al. ................ 424/9.4
2008/0277350 A1 * 11/2008 Roesch et al. ................. 210/682

FOREIGN PATENT DOCUMENTS

WO    WO 2011/106846    *    9/2011    ............. C01G 15/00

OTHER PUBLICATIONS

Liu et al., Bioconjugate Chem. (2003) 14, 1052-1056.*
Decristoforo et al., Nuclear Medicine Communications (2007) 28, 870-875.*
Breeman et al., Eur J Nucl Med Mol Imaging (2002) 32, 478-485.*
See Sigma-Aldrich Bulletin 862—TSK-GEL Nonporous Resin Columns.*
See Sigma-Aldrich Bulletin 862—TSK-GEL Nonporous Resin Columns, 1996.*
Canadian Examination Report, mailing date Jun. 23, 2014, from corresponding Canadian Application No. 2,816,070.
Canadian Examination Report, mailing date Feb. 27, 2015, from corresponding Canadian Application No. 2,816,070.

* cited by examiner

*Primary Examiner* — Karlheinz R Skowronek
*Assistant Examiner* — Catherine Mader
(74) *Attorney, Agent, or Firm* — Intellectual Property Law Group LLP

(57) ABSTRACT

The invention relates to a method and a kit for preparing a radiopharmaceutical, the method comprising the steps:

elution of a $^{68}$Ge/$^{68}$Ga-Generator using hydrochloric acid as an eluent for obtaining a generator eluate comprising $^{68}$Gallium, feeding the generator eluate through a cation exchange cartridge, which collects the $^{68}$Gallium, separating the used eluent, eluting the $^{68}$Gallium from the cation exchange cartridge using a solution comprising sodium chloride and hydrochloric acid and feeding the resulting eluate into an aqueous precursor mixture comprising at least a labelling precursor thereby forming a reaction solution.

20 Claims, 1 Drawing Sheet

METHOD AND KIT FOR PREPARING A RADIOPHARMACEUTICAL

TECHNICAL FIELD

The invention relates to a method and a kit for preparing a radiopharmaceutical.

BACKGROUND OF THE INVENTION

Functional imaging for medical diagnostics has been used for decades. In some functional imaging methods, e.g. PET (positron emission tomography) or SPECT (single-photon emission computed tomography) peptides such as Edotreotid (DOTATOC) are marked with radionuclides such as $^{68}$Gallium and used as radiopharmaceuticals (also referred to as tracers). When introduced into the human body the radiopharmaceutical binds to certain receptors which are particularly numerous in tumor cells. The functional imaging can detect and localize the increased beta-plus-decay of the $^{68}$Gallium. According to [I. Velikyan: *Synthesis, Characterisation and Application of $^{68}$Ga-labelled Macromolecules*. Dissertation, University Uppsala, 2005] the isotope $^{68}$Gallium decays with a radioactive half-life of 67.629 minutes in a proportion of 89% by emitting a positron with at most 1.9 MeV and of 11% by catching electrons; thereby respectively creating the daughter isotope $^{68}$Zink. In nuclear medical applications the emitted positron hits an electron after travelling a few millimeters so that both annihilate and create two photons with 511 keV each, wherein both photons are emitted at a relative angle of nearly 180° from the point of annihilation. The emitted photons can be detected by appropriate detectors. Reconstructing a number of detection events allows for quite precisely localising the point of annihilation.

Due to the short half-life of $^{68}$Gallium, the radiopharmaceutical cannot be shelved over long time periods but has to be prepared at relatively short notice prior to the intended application.

$^{68}$Gallium is generated by means of so called $^{68}$Gallium-generators, also referred to as $^{68}$Ge/$^{68}$Ga-generators, from $^{68}$Germanium. $^{68}$Germanium has a half life of 270.8 days and decays into the daughter isotope $^{68}$Gallium, which concentrates in the generator until reaching a cut-off concentration determined by its own decay. The generated $^{68}$Gallium is eluted by a solvent fed into the generator. The solvent eluting only Gallium but not Germanium, separates Gallium out of the stationary phase from the parent isotope $^{68}$Germanium.

Known methods use hydrochloric acid with a normality from 0.05 N to 0.4 N for elution, wherein the elution volume is between 5 ml and 10 ml. The eluate is therefore hydrochloric and cannot be directly used for labelling peptides.

This problem has been tackled by different approaches.

In a method known as anionic concentration, the eluate is mixed with a large volume of concentrated hydrochloric acid, $^{68}$Ga is then collected by an anion exchanger and subsequently eluted by means of water into a HEPES (4-(2-hydroxyethyl)-1-piperazineethanesulfonic acid) buffer solution for labelling peptides or other ligands. This method requires a subsequent purification of the product, i.e. separation of unwanted substances. Furthermore, the method requires handling of large quantities of concentrated hydrochloric acid.

Another established method is the combined cationic/anionic concentration, wherein a cation exchange cartridge (SCX—strong cation exchanger) and an anion exchange cartridge (SAX—strong anion exchanger) are used.

In the cationic concentration of $^{68}$Gallium the $^{68}$Gallium is collected using a cation exchanger (SCX) and subsequently eluted with an acetone/hydrochloric acid solution. The obtained reaction mixture therefore contains acetone which has to be removed by distilling at temperatures of more than 90° C. prior to application of the product to the human body. The use of acetone requires additional quality control testing of the final product such as gas chromatography.

There remains a need for a kit for improved preparation of a radiopharmaceutical and for a respectively improved method for preparation of a radiopharmaceutical.

SUMMARY OF THE INVENTION

The object is achieved by a method according to claim 1 and by a kit according to claim 13.

Advantageous embodiments are given in the dependent claims.

According to the invention, a method for preparing a radiopharmaceutical comprises the steps:

elution of a $^{68}$Ge/$^{68}$Ga-Generator using hydrochloric acid as an eluent for obtaining a generator eluate comprising $^{68}$Gallium, feeding the generator eluate through a cation exchange cartridge, which collects the $^{68}$Gallium, separating the used eluent, which may contain generator waste, e.g. breakthrough of the parent isotope $^{68}$Ge, eluting the $^{68}$Gallium from the cation exchange cartridge using a solution comprising sodium chloride and hydrochloric acid and feeding the resulting eluate into an aqueous precursor mixture comprising at least a labelling precursor thereby forming a reaction solution.

The contents of the reaction solution are now complete and the labelling reaction, in which the $^{68}$Gallium binds with the labelling precursor, is allowed to start or will start right away.

In an exemplary embodiment a buffer solution at least comprising a buffer compound may be used to adjust the pH value of the reaction solution between 3 and 4.

The buffer compound may be a buffer salt, such as one of sodium acetate and ammonium acetate. Further buffer components may be acetic acid and hydrochloric acid. Likewise HEPES may be used as the buffer compound.

In an exemplary embodiment the reaction mixture may be prepared by dissolving a lyophilized precursor mixture of the labelling precursor and the buffer salt using a solvent.

In an exemplary embodiment the solvent is an aqueous solution of the buffer components acetic acid and hydrochloric acid.

In an exemplary embodiment the hydrochloric acid and acetic acid in the solvent are provided in such an amount that, taking into account the amount of buffer salt, the pH value of the solution of the mixture of the contents of the reaction vial, the solvent of the solvent vial and the elution solution of the elution vial used for eluting the SCX cartridge is between 3 and 4.

In an exemplary embodiment the cation exchange cartridge is silica gel based.

In an exemplary embodiment of the cation exchange cartridge is pre-conditioned with hydrochloric acid and water.

In an exemplary embodiment the reaction solution is heated to a temperature of 90° C. to 100° C. over a time period of 5 minutes to 15 minutes, in particular seven minutes.

In an exemplary embodiment the radiopharmaceutical is neutralized by adding a phosphate buffer.

In an exemplary embodiment the labelling precursor is selected from a group comprising ethylenediamine tetra(methylene phosphonic acid), ligand conjugated peptides, DOTA-conjugated peptides, DOTATOC, NODAGA-conjugated peptides, DOTATATE, macroaggregated human serum albumin, diethylene triamine pentaacetic acid.

In an exemplary embodiment the method may be performed using a kit.

The kit for preparing a radiopharmaceutical comprises:
a cation exchange cartridge,
a reaction vial with a labelling precursor, in particular a lyophilized labelling precursor,
a solvent vial with a solvent comprising a aqueous solution of acetic acid and hydrochloric acid,
an elution vial with a solution comprising sodium chloride and hydrochloric acid,
a buffer salt.

The buffer salt may be comprised in the reaction vial or the solvent vial.

The contents of all vials may be sterile.

The contents of the reaction vial may be lyophilized.

In an exemplary embodiment the kit further comprises a vial with a sodium phosphate buffer.

In an exemplary embodiment of the hydrochloric acid and acetic acid in the solvent are provided in such an amount that, taking into account the amount of buffer salt, the pH value of the contents of the reaction vial, the solvent of the solvent vial and the elution solution of the elution vial used for eluting the SCX cartridge is between 3 and 4.

In an exemplary embodiment the labelling precursor is selected from a group comprising ethylenediamine tetra(methylene phosphonic acid), ligand conjugated peptides, DOTA-conjugated peptides, DOTATOC, NODAGA-conjugated peptides, DOTATATE, human serum albumin, diethylene triamine pentaacetic acid.

The cation exchange cartridge (SCX-cartridge) may be a sterile cation exchange cartridge.

A vial may also be referred to as an ampoule or a septum flask.

In an exemplary embodiment lyophilized ascorbic acid or another suitable stabilizer may be provided in the reaction vial. The stabilizer prevents radiolytic degradation of the marked substance when using the radiopharmaceutical.

In an exemplary embodiment ammonium acetate or sodium acetate may be used as the buffer salt.

The kit may be applied as follows:

A $^{68}$Ge/$^{68}$Ga generator generates the $^{68}$Gallium required for labelling. The $^{68}$Ge/$^{68}$Ga generator is eluted by hydrochloric acid, e.g. with a concentration of 0.1 mol/l. Thus $^{68}$Gallium is eluted. The resulting generator eluate is fed through the SCX cartridge. The SCX cartridge may be silica gel based. The SCX cartridge may be pre-conditioned with 1 ml hydrochloric acid (5.5 mol/l) and 10 ml water. The lyophilized mixture in the reaction vial is dissolved by the solvent of the solvent vial. The SCX cartridge is then eluted into the reaction vial using the solution of the elution vial.

The resulting reaction solution in the reaction vial may optionally be heated to a temperature of 90° C. to 100° C., for example over a time period of 5 minutes to 15 minutes, in particular seven minutes, in order to accelerate the reaction, in which the $^{68}$Gallium binds with the labelling precursor for forming the tracer. The reaction may likewise take place at ambient temperature; however, this may require more time.

In the tracer the concentration of free $^{68}$Gallium is preferably lower than 5%. Die radiopharmaceutical purity of the tracer is higher than 95%. Subsequent purification is not required. After the final reaction mixture has been optionally subjected to sterile filtering the radiopharmaceutical yield is approximately 82% (n.d.c.—non decay corrected).

At the end of the reaction the radiopharmaceutical or tracer may be neutralized by adding a sterile phosphate buffer, e.g. 2 ml sodium phosphate 1 mmol/ml Na$^+$, 0.6 mmol/ml PO$_4^{3-}$, pH=7.0.

The tracer may be subjected to a thin layer chromatographic quality check. The final reaction solution may be used directly without additional purification as a radiopharmaceutical.

The kit and the method may be routinely applied in clinical practise when performing $^{68}$Ga labelling methods. The kit and the method reduce handling of concentrated hydrochloric acid when purifying and concentrating the $^{68}$Ga eluate. The final product (tracer) can be obtained with a high purity and high yield of approximately 80% to 95%. Use of acetone or other organic solvents and compounds like HEPES may be likewise avoided by the kit and the method. Thus, other than in conventional methods, verification of full removal of acetone by elaborate quality checks, e.g. by means of a gasphase chromatograph, is not required. Thus, production of kits is enabled, which may be applied by medical staff in a simple manner by adding the solvent to the lyophilized mixture so that expensive laboratory equipment is not required.

The resulting tracers are stable over longer time periods than tracers known in the art. Thus multi dose preparations for labelling and examining a number of patients may be prepared.

In an exemplary embodiment the labelling precursor is the ligand ethylenediamine tetra(methylene phosphonic acid) (EDTMP), which is the labelling precursor. The tracer resulting from application of this labelling precursor in the method may be used in particular for bone scintigraphy.

In another exemplary embodiment the labelling precursor is a ligand conjugated peptide, for example DOTA-(1,4,7,10-Tetraazacyclododecan-1,4,7,10-tetra acetic acid) or NODAGA-conjugated peptids, in particular DOTATOC (edotreotide) or DOTATATE (DOTA-[Tyr$^3$]octreotate). The tracer resulting from application of this labelling precursor in the method may be used in particular for diagnosing neuroendocrine tumors by PET.

In yet another exemplary embodiment the labelling precursor is macroaggregated human serum albumin (HSA). The tracer resulting from application of this labelling precursor in the method may be used in particular for perfusion diagnosis using PET.

In yet another exemplary embodiment the labelling precursor is DTPA (diethylene triamine pentaacetic acid). The tracer resulting from application of this labelling precursor in the method may be used in particular for functional diagnosis of the kidney using PET.

Sodium acetate may be substituted by ammonium acetate. However, sodium acetate is preferred as it is better suited for lyophilisation.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

Figure 1:
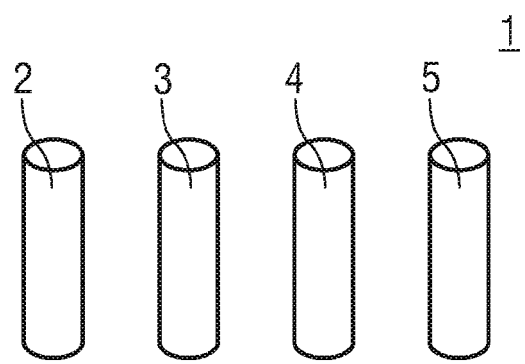
FIG. 1 is a schematic view of a kit for preparing a radiopharmaceutical.

REFERENCE NUMERALS 1 kit
2 cation exchange cartridge
3 reaction vial
4 solvent vial
5 elution vial
6 $^{68}$Ge/$^{68}$Ga generator
7 sterile filter
8 radiopharmaceutical
9 waste container

DETAILED DESCRIPTION OF PREFERRED EMBODIMENTS

FIG. 1 is a schematic view of a kit 1 for preparing a radiopharmaceutical. The kit 1 comprises:
a cation exchange cartridge 2,
a reaction vial 3 with a reaction mixture comprising a labelling precursor and a buffer salt,
a solvent vial 4 with a solvent,
an elution vial 5 with a sterile solution comprising sodium chloride NaCl and hydrochloric acid HCl.

In a first embodiment the labelling precursor in the reaction vial 3 is ethylenediamine tetra(methylene phosphonic acid) (EDTMP). The radiopharmaceutical 8 resulting from application of this reaction vial in the method may be used in particular for bone scintigraphy.

In the first embodiment the reaction vial 3 comprises:
at most 10 mg, preferably at most 1 mg ethylenediamine tetra(methylene phosphonic acid) (EDTMP),
23 mg to 40 mg, preferably 27.6 mg buffer salt, preferably sodium acetate $C_2H_3NaO_2$,
at most 100 mg, preferably at most 5 mg L-ascorbic acid $C_6H_8O_6$ In the first embodiment the solution vial 4 comprises:
1 ml to 10 ml, preferably 1 ml to 7 ml water $H_2O$
5 µl to 10 µl, preferably 6.73 µl concentrated hydrochloric acid HCl
5 µl to 10 µl, preferably 7 µl to 8 µl acetic acid $C_2H_4O_2$.

In the first embodiment the elution vial 5 comprises an amount of 0.25 ml to 3 ml elution solution of 5 mol/l sodium chloride NaCl and 5.5 mol/l hydrochloric acid HCl with 13 µl to 100 µl, preferably 25 µl 5.5 mol/l hydrochloric acid HCl per ml 5 mol/l sodium chloride NaCl.

In a second embodiment the labelling precursor in the reaction vial is a DOTA-(1,4,7,10-Tetraazacyclododecan-1,4,7,10-tetra acetic acid) or NODAGA-conjugated peptide, in particular DOTATOC (edotreotide) or DOTATATE (DOTA-[Tyr$^3$]octreotate). The radiopharmaceutical 8 resulting from application of this labelling precursor in the method may be used in particular for diagnosing neuro-endocrine tumors by PET.

In the second embodiment the reaction vial 3 comprises:
at most 1 mg, preferably 15 µg to 100 µg of the conjugated peptide,
20 mg to 40 mg, preferably 27.6 mg buffer salt, particularly sodium acetate $C_2H_3NaO_2$,
at most 100 mg, preferably at most 5 mg L-ascorbic acid $C_6H_8O_6$ In the second embodiment the solvent vial 4 comprises:
1 ml to 10 ml, preferably 1 ml to 3 ml water $H_2O$
2 µl to 10 µl, preferably 6.73 µl concentrated hydrochloric acid HCl
2 µl to 10 µl, preferably 4 µl to 8 µl acetic acid $C_2H_4O_2$.

In the second embodiment the elution vial 5 comprises an amount of 0.25 ml to 3 ml elution solution comprising 5 mol/l sodium chloride NaCl and 5.5 mol/l hydrochloric acid HCl with 10 µl to 100 µl, preferably 25 µl 5.5 mol/l hydrochloric acid HCl per ml 5 mol/l sodium chloride NaCl.

In a third exemplary embodiment the labelling precursor is human serum albumin HSA, preferably macroaggregated HSA. The radiopharmaceutical 8 resulting from application of this labelling precursor in the method may be used in particular for perfusion diagnosis using PET.

In the third embodiment the reaction vial 3 comprises:
at most 20 mg, preferably at most 2 mg macroaggregated human serum albumin HSA,
22 mg to 40 mg, preferably 27.6 mg buffer salt, particularly sodium acetate $C_2H_3NaO_2$,
at most 100 mg, preferably at most 5 mg L-ascorbic acid $C_6H_8O_6$ In the third embodiment the solvent vial 4 comprises:
1 ml to 10 ml, preferably 1 ml to 7 ml water $H_2O$
4 µl to 10 µl, preferably 6.73 µl concentrated hydrochloric acid HCl
4 µl to 10 µl, preferably 6 µl to 8 µl acetic acid $C_2H_4O_2$.

In the third embodiment the elution vial 5 contains an amount of 0.25 ml to 3 ml elution solution comprising 5 mol/l sodium chloride NaCl and 5.5 mol/l hydrochloric acid HCl with 12 µl to 100 µl, preferably 25 µl 5.5 mol/l hydrochloric acid HCl per ml 5 mol/l sodium chloride NaCl.

In a fourth exemplary embodiment the labelling precursor is diethylene triamine pentaacetic acid DTPA. The radiopharmaceutical 8 resulting from application of this labelling precursor in the method may be used in particular for functional diagnosis of the kidney using PET.

In the fourth embodiment the reaction vial 3 comprises:
at most 10 mg, preferably 0.5 mg to 5 mg diethylene triamine pentaacetic acid DTPA,
21 mg to 40 mg, preferably 27.6 mg buffer salt, preferably sodium acetate $C_2H_3NaO_2$,
at most 100 mg, preferably at most 5 mg L-ascorbic acid $C_6H_8O_6$ In the fourth embodiment the solvent vial 4 comprises:
1 ml to 10 ml, preferably 1 ml to 7 ml water $H_2O$
3 µl to 10 µl, preferably 6.73 µl concentrated hydrochloric acid HCl
3 µl to 10 µl, preferably 5 µl to 8 µl acetic acid $C_2H_4O_2$.

In the fourth embodiment the elution vial 5 comprises an amount of 0.25 ml to 3 ml elution solution comprising 5 mol/l sodium chloride NaCl and 5.5 mol/l hydrochloric acid HCl with 11 µl to 100 µl, preferably 25 µl 5.5 mol/l hydrochloric acid HCl per ml 5 mol/l sodium chloride NaCl.

The following statements apply to all embodiments regardless of the labelling precursor used.

The mixture in the reaction vial 3 is lyophilized.

The mixture in the reaction vial 3 optionally comprises ascorbic acid $C_6H_8O_6$ or a different scavenger.

The solvent may be an aqueous solution of acetic acid $C_2H_4O_2$ and hydrochloric acid HCl.

The buffer salt is ammonium acetate $CH_3COONH_4$ or sodium acetate $C_2H_3NaO_2$.

The SCX cartridge 2 may be pre-conditioned with hydrochloric acid HCl and water $H_2O$, particularly with 1 ml 5.5 mol/l hydrochloric acid HCl and 10 ml water $H_2O$.

The kit 1 may additionally comprise a vial with a neutralizing buffer, preferably a sodium phosphate buffer.

Figure 2:
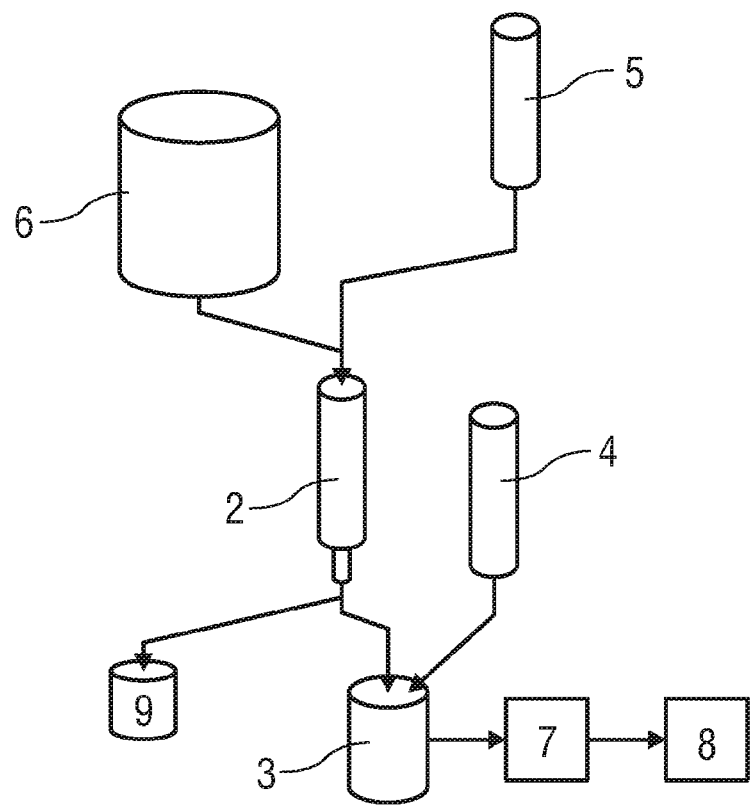
FIG. 2 is a schematic view of an arrangement for preparing a radiopharmaceutical using the kit.

FIG. 2 is a schematic view of an arrangement for preparing a radiopharmaceutical 8 using the kit 1.

A $^{68}Ge/^{68}Ga$ generator 6 provides the $^{68}Gallium$ required for labelling. The $^{68}Ge/^{68}Ga$-Generator 6 is eluted using hydrochloric acid HCl, e.g. with a concentration of 0.1 mol/l. Thus, $^{68}Gallium$ is eluted, fed through the cation exchange cartridge 2 and trapped there. The 0.1 mol/l HCl having been used for eluting the generator 6, which may contain the generator breakthrough of the parent isotope $^{68}Germanium$ is collected separately in a waste container 9 and disposed of according to the applicable legal regulations. The lyophilized mixture in the reaction vial 3 is dissolved by the solvent from the solvent vial 4. The cation exchange cartridge 2 is subsequently eluted into the reaction vial 3 using the solution from the elution vial 5.

The resulting reaction solution in the reaction vial 3 may optionally be heated to a temperature of 90° C. to 100° C., for example over a time period of 5 minutes to 15 minutes, particularly seven minutes, in order to accelerate the reaction, in which the $^{68}Gallium$ binds to the labelling precursor for forming the radiopharmaceutical 8 or tracer. The reaction may likewise take place at ambient temperature; however, this may require more time.

At the end of the reaction a sterile phosphate buffer may be added.

The reaction product may optionally be filtered by a sterile filter 7.

The prepared tracer may subsequently be used as radiopharmaceutical 8.

The method for preparing the radiopharmaceutical 8 may be performed using the kit 1 or without the kit 1. The method may likewise be performed with an aqueous reaction mixture without having to dissolve a lyophilized reaction mixture first.

What is claimed is:

1. A method for preparing a radiopharmaceutical comprising the steps:
   elution of a $^{68}Ge/^{68}Ga$-Generator using hydrochloric acid as an eluant for obtaining a generator eluate comprising $^{68}Gallium$,
   feeding the generator eluate through a cation exchange cartridge, which collects the $^{68}Gallium$, and separates the $^{68}Gallium$ from the used eluent,
   eluting the collected $^{68}Gallium$ from the cation exchange cartridge using a solution comprising sodium chloride and hydrochloric acid, and feeding the resulting eluate, into an aqueous precursor mixture comprising at least a labelling precursor thereby forming a reaction solution requiring no subsequent purification,
   wherein the solution for eluting the collected $^{68}Gallium$ from the cation exchange cartridge follows directly after the generator eluate is fed through the cation exchange cartridge, and
   wherein the entire method is devoid of using organic solvents.

2. The method of claim 1, wherein a buffer solution at least comprising a buffer compound is used to adjust the pH value of the reaction solution between 3 and 4.

3. The method of claim 2, wherein the buffer solution comprises a buffer salt, acetic acid and hydrochloric acid.

4. The method of claim 3, wherein one of sodium acetate and ammonium acetate is used as the buffer salt.

5. The method of claim 3, wherein the reaction mixture is prepared by mixing a lyophilized precursor mixture of the labelling precursor and the buffer salt using a solvent.

6. The method of claim 5, wherein the solvent is an aqueous solution of the buffer components acetic acid and hydrochloric acid.

7. The method of claim 1, wherein the precursor mixture comprises a stabilizer for preventing radiolytic degradation of the radiopharmaceutical.

8. The method of claim 7, wherein the stabilizer is ascorbic acid.

9. The method of claim 1, wherein the cation exchange cartridge is silica gel based.

10. The method of claim 1, wherein the reaction solution is heated to a temperature of 90° C. to 100° C. over a time period of 5 minutes to 15 minutes, in particular seven minutes.

11. The method of claim 1, wherein the radiopharmaceutical is neutralized by adding a phosphate buffer.

12. The method of claim 1, wherein the labelling precursor is selected from a group comprising ethylenediamine tetra (methylene phosphonic acid), ligand conjugated peptides, DOTA-conjugated peptides, DOTATOC, NODAGA-conjugated peptides, DOTATATE, macroaggregated human serum albumin, diethylene triamine pentaacetic acid.

13. A kit for preparing a radiopharmaceutical comprising:
   a cation exchange cartridge,
   a reaction vial with a labelling precursor,
   a solvent vial with a solvent comprising an aqueous solution of acetic acid and hydrochloric acid,
   an elution vial with a solution comprising sodium chloride and hydrochloric acid,
   a buffer salt,
   wherein the kit is configured to entirely avoid organic solvents.

14. The kit of claim 13, wherein the buffer salt is contained in the reaction vial or in the solvent vial.

15. The kit of claim 13, wherein the content of the reaction vial is lyophilized.

16. The kit of claim 13, wherein the reaction mixture comprises a stabilizer.

17. The kit of claim 16, wherein the stabilizer comprises ascorbic acid.

18. The kit of claim 13, wherein the buffer salt is one of ammonium acetate and sodium acetate.

19. The kit of claim 13, wherein the buffer components hydrochloric acid and acetic acid in the solvent are provided in such an amount that, taking into account the amount of buffer salt, the pH value of the contents of the reaction vial, the solvent of the solvent vial and the elution solution of the elution vial used for eluting the SCX cartridge is between 3 and 4.

20. The kit of claim 13, wherein the labelling precursor is selected from a group comprising ethylenediamine tetra(methylene phosphonic acid), ligand conjugated peptides, DOTA-conjugated peptides, DOTATOC, NODAGA-conjugated peptides, DOTATATE, macroaggregated human serum albumin, diethylene triamine pentaacetic acid.

* * * * *